(12) United States Patent
Shin et al.

(10) Patent No.: US 9,072,525 B2
(45) Date of Patent: Jul. 7, 2015

(54) COMBINABLE ELECTRODE NEEDLE BASE STRUCTURE

(75) Inventors: Kyung-Min Shin, Seoul (KR);
Kyung-Hoon Shin, Gyeonggi-do (KR);
Kil-Soo Kim, Gyeonggi-do (KR);
Dong-Un Kim, Gyeonggi-do (KR)

(73) Assignees: Taewoong Medical Co., Ltd., Gimpo, Gyeonggi-Do (KR); Kyung-Min Shin, Seoul (KR)

( * ) Notice: Subject to any disclaimer, the term of this patent is extended or adjusted under 35 U.S.C. 154(b) by 798 days.

(21) Appl. No.: 13/383,903

(22) PCT Filed: Jan. 21, 2011

(86) PCT No.: PCT/KR2011/000450
§ 371 (c)(1),
(2), (4) Date: Jan. 13, 2012

(87) PCT Pub. No.: WO2011/090350
PCT Pub. Date: Jul. 28, 2011

(65) Prior Publication Data
US 2012/0179152 A1      Jul. 12, 2012

(30) Foreign Application Priority Data

Jan. 21, 2010  (KR) .................. 10-2010-0005511

(51) Int. Cl.
*A61B 18/18* (2006.01)
*A61B 18/14* (2006.01)
*A61H 39/00* (2006.01)
*A61H 39/08* (2006.01)
*A61B 18/00* (2006.01)

(52) U.S. Cl.
CPC ......... *A61B 18/1477* (2013.01); *A61B 18/1402* (2013.01); *A61B 2018/0016* (2013.01); *A61B 2018/143* (2013.01); *A61H 39/002* (2013.01); *A61H 39/086* (2013.01)

(58) Field of Classification Search
CPC ........... A61N 1/06; A61N 2018/00005; A61N 2018/00166; A61N 2018/00577; A61N 2018/00595; A61N 2018/00702; A61N 2018/1246; A61N 2018/125; A61N 2018/126; A61B 5/0408; A61B 5/0485; A61B 5/0422; A61B 5/0492; A61B 18/08; A61B 18/082; A61B 18/12; A61B 18/1206; A61B 18/14; A61B 18/1467; A61B 18/1477; A61B 18/1405; A61B 18/1495; A61B 18/1425; A61B 18/143; A61B 18/1492; A61B 2018/00005; A61B 2018/00166; A61B 2018/00577; A61B 2018/00595; A61B 2018/00702; A61B 2018/1246; A61B 2018/125; A61B 18/1402; A61B 2018/0016; A61B 2018/143; A61H 39/002; A61H 39/086
See application file for complete search history.

(56) References Cited

U.S. PATENT DOCUMENTS

| | | | |
|---|---|---|---|
| 6,530,922 B2 * | 3/2003 | Cosman et al. | 606/34 |
| 2005/0085807 A1 | 4/2005 | Venturelli | |
| 2007/0167749 A1 * | 7/2007 | Yarnall et al. | 600/431 |
| 2007/0250053 A1 | 10/2007 | Fernald et al. | |
| 2009/0306652 A1 * | 12/2009 | Buysse et al. | 606/41 |

FOREIGN PATENT DOCUMENTS

| | | |
|---|---|---|
| CN | 1147964 A | 4/1997 |
| JP | 06190059 A | 7/1994 |
| JP | 11267227 A | 10/1999 |
| JP | 2004160083 A | 6/2004 |
| JP | 2007244748 A | 9/2007 |
| KR | 10-2009-0105509 | 10/2009 |
| WO | 9421168 A1 | 9/1994 |
| WO | 9604860 A1 | 2/1996 |

OTHER PUBLICATIONS

Chinese Office Action Issued Dec. 30, 2013 in connection with corresponding Chinese Patent Application No. 201180002715.5.

* cited by examiner

*Primary Examiner* — Christopher D Koharski
*Assistant Examiner* — Frances Oropeza

(74) *Attorney, Agent, or Firm* — Locke Lord LLP; Christopher J. Capelli; Judy Naamat

(57) ABSTRACT

Provided is a combinable electrode needle base structure in which a base to which electrode needles are coupled can be used in a combined or separated state to use the electrode needles according to the size and location of a lesion. In the combinable electrode needle structure, electrode needles are connected to the front side of an electrode needle base, and receive RF waves from RF (radio frequency) generator. The electrode needle base is divided into dividable bases to which the electrode needles are respectively coupled. When a lesion to be cauterized is large or cauterization should be concentrated, the dividable bases are combined and then used, and when a lesion is small or lesions are scattered, the dividable bases may be separated and then used.

2 Claims, 5 Drawing Sheets

COMBINABLE ELECTRODE NEEDLE BASE STRUCTURE

CROSS-REFERENCES TO RELATED APPLICATIONS

This application is a 35 U.S.C. §371 U.S. national entry of International Application PCT/KR2011/000450 (WO 2011/090350) having an International filing date of Jan. 21, 2011, which claims under 35 U.S.C. §119(a) the benefit of Korean Application No. 10-2010-0005511, filed Jan. 21, 2010, the entire contents of which are incorporated herein by reference.

TECHNICAL FIELD

The present invention relates to a combinable electrode needle base structure, and more particularly, to a combinable electrode needle base structure in which a base to which electrode needles are coupled can be used in a combined state or in a separated state according to the size and location of a lesion to be cauterized (or ablated).

BACKGROUND ART

Generally, tumorous tissue within an organ such as the liver is either treated via a non-surgical method or surgical method.

Examples of common non-surgical treatment methods include transarterial chemoembolization (TACE), percutaneous ethanol injection therapy (PEIT), systemic chemotherapy, partial heat treatment (local thermotherapy). Among these treatment methods, partial heat treatment is known as the most effective.

Partial heat treatment includes RFA (radio frequency ablation) (including microwave ablation), laser ablation, and the like, and among them, thermal treatment using RF waves (including high frequency and microwave) is favored by doctors or patients because it is considered to be the most effective treatment.

According to RFA, it is unnecessary to remove part of an organ such a liver to treat tumorous tissue therein. That is, tumorous tissue can be selectively cauterized by using heat generated by RF waves (including high frequency and microwave).

In an electrode device for RFA, an electrode line and a coolant line are connected to a grip base to supply RF waves and coolant, and an electrode needle is coupled to the front side of the grip base. The electrode needle of the electrode device is inserted into a lesion such as tumorous tissue within an organ, and if RF waves are supplied from an RF generator to the electrode needle, a conductive part of the electrode receives the RF waves while an insulating part of the electrode needle does not receive the RF waves. Then, the lesion is cauterized by heat generated due to the RF waves.

A single electrode needle or a plurality of non-separable electrode needles are coupled to the grip base. When the size of a lesion is small, a single electrode needle is usually used, while when the size of a lesion is large, a plurality of electrode needles are used. However, when lesions are scattered, additional electrode needles are necessary.

Therefore, there is a need for an electrode device including a grip base that can be separated into parts to which electrode needles are respectively coupled so that the electrode device can be used in various states according to the size and scattering of lesions.

DISCLOSURE OF INVENTION

Technical Problem

An aspect of the present invention provides a combinable electrode needle base structure including an electrode needle base that can be used in a combined state or a separated state to use electrode needles according to the size and scattering of lesions.

Another aspect of the present invention provides a combinable electrode needle base structure including a combinable electrode needle base so that a plurality of electrode needles can be used together or individually by combining or separating the electrode needle base.

Another aspect of the present invention provides a combinable electrode needle base structure including an electrode needle base which can be combined by using coupling tools so as to prevent separation.

Solution to Problem

According to an aspect of the present invention, there is provided a combinable electrode needle base structure comprising an electrode needle base, the electrode needle base including a front side to which electrode needles are coupled, so as to receive RF waves from RF (radio frequency) generator, wherein the electrode needle base is divided into a plurality of dividable bases to which the electrode needles are respectively coupled, and coupling parts which do not interface with each other are formed on separation surfaces of each of the dividable bases so that the coupling parts of the separation surfaces of one dividable base are coupled to the coupling parts of the separation surfaces of another dividable base, wherein the combinable electrode needle base structure is used in a combined state by coupling the coupling parts of the separation surfaces of one dividable base to the coupling parts of the separation surfaces of another dividable base, or the combinable electrode needle base structure is used in a separated state by decoupling the coupling parts of the separation surfaces of one dividable base from the coupling parts of the separation surfaces of another dividable base.

Widened parts may be formed on both ends of each of the dividable bases, wherein when the dividable bases are combined, coupling tools may be coupled to outer sides of the dividable bases in a manner such that the coupling tools cover and fasten the widened parts of the dividable bases so as to prevent separation of the dividable bases.

The combinable electrode needle base structure may further include a guide, wherein the guide may include guide stages having different heights, and penetration holes may be formed through the guide stages to receive the electrode needles.

Advantageous Effects of Invention

According to the present invention, the electrode needles can be used together or individually by combining or separating the electrode needle base according to the size and scattering of lesions. Therefore, additional electrode needles are not necessary according the states of lesions.

In addition, since the electrode needles can be used together by combining the electrode needle base or individually by separating the electrode needle base, the combinable electrode needle base structure can be used under various conditions.

In addition, since the coupling tools are used when combining the electrode needle base, the electrode needle base can be stably maintained in the combined state.

BRIEF DESCRIPTION OF DRAWINGS

The above and other aspects, features and other advantages of the present invention will be more clearly understood from the following detailed description taken in conjunction with the accompanying drawings, in which.

MODE FOR THE INVENTION

Figure 1:
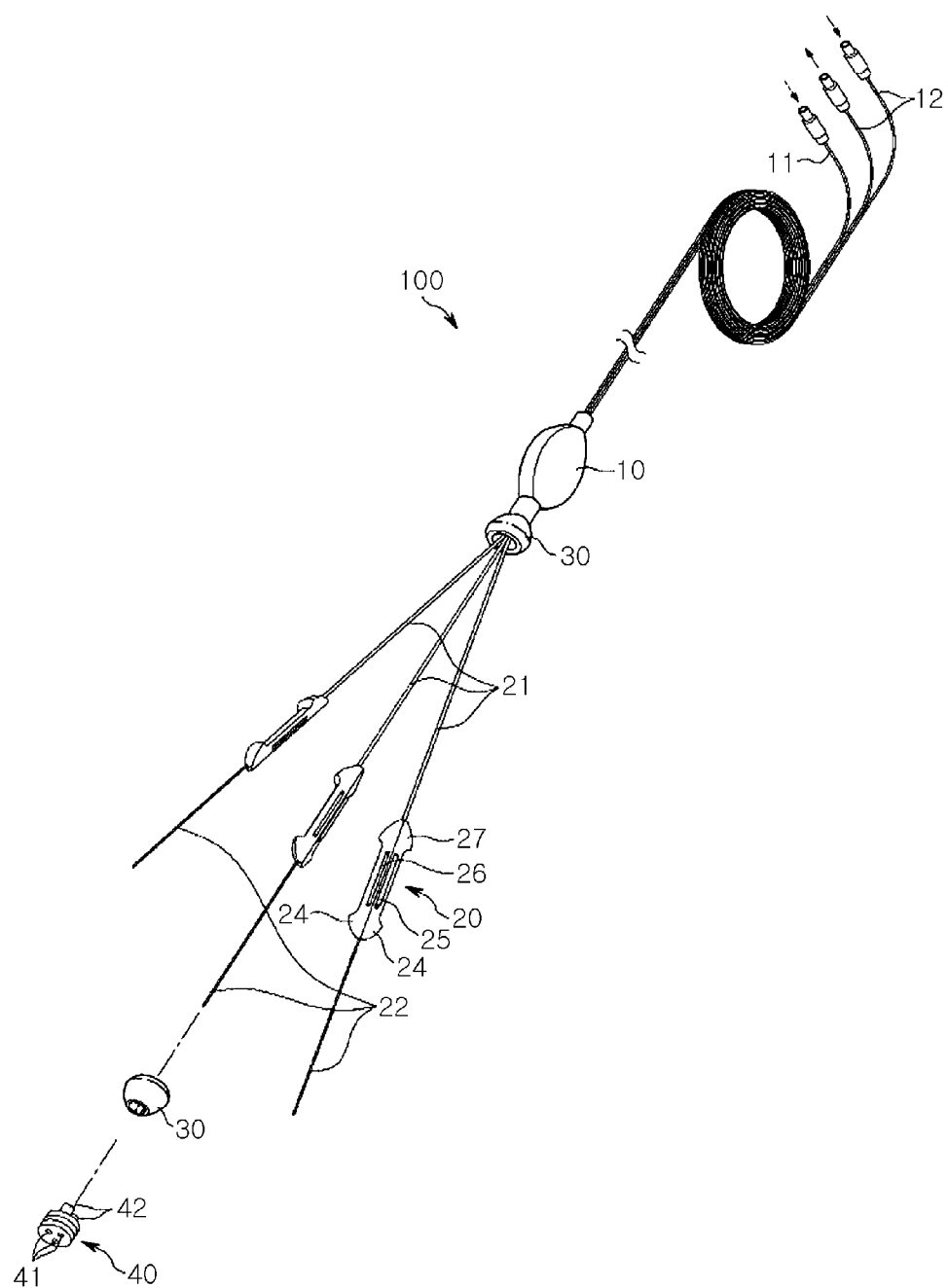
FIG. 1 is a perspective view illustrating a combinable electrode needle base structure according to an embodiment of the present invention
Figure 2:
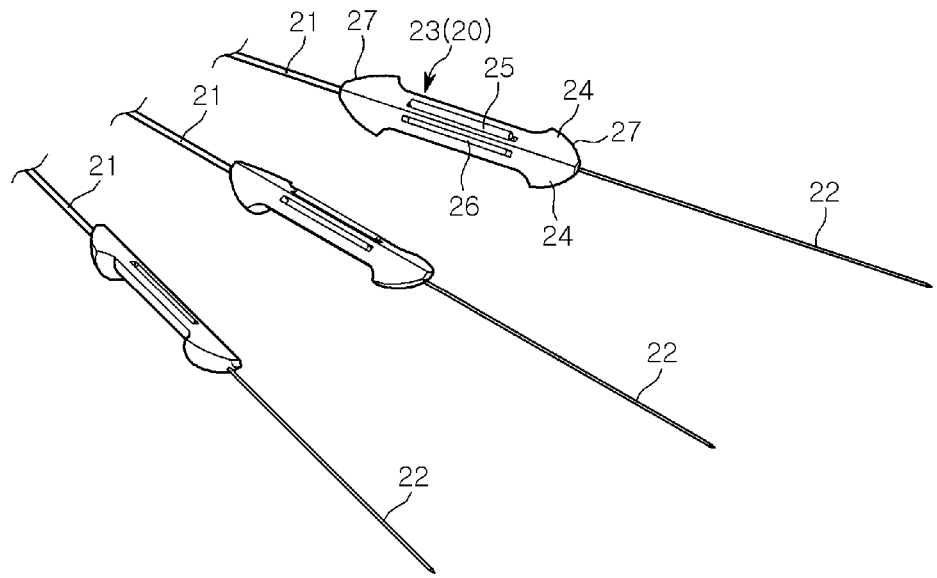
FIG. 2 is an exploded perspective view illustrating a separated state of an electrode needle base according to an embodiment of the present invention
Figure 3:
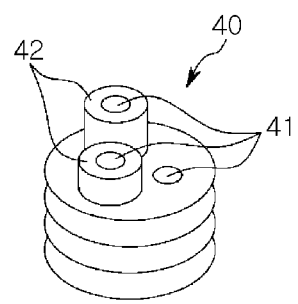
FIG. 3 is a perspective view illustrating a guide according to an embodiment of the present invention
Figure 4:
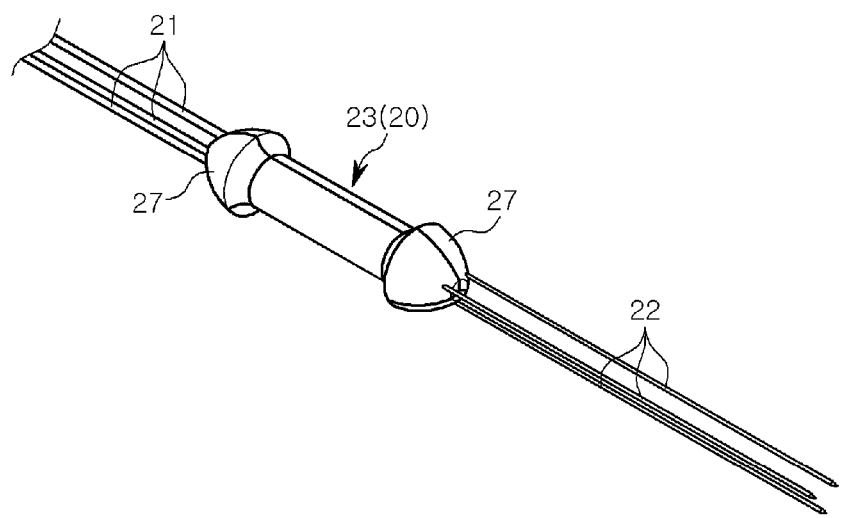
FIG. 4 is a perspective view illustrating a combined state of the electrode needle base according to an embodiment of the present invention.
Figure 5:
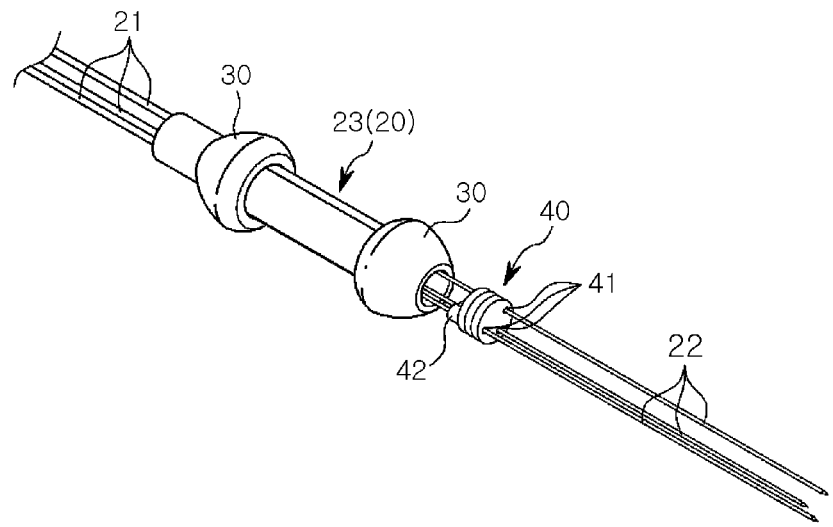
FIG. 5 is a perspective view illustrating a state where coupling tools and the guide are coupled to the combined electrode needle base of FIG. 4, according to an embodiment of the present invention

Exemplary embodiments of the present invention will now be described in detail with reference to the accompanying drawings.

As shown in FIGS. 1 through 5, in a combinable electrode needle base structure 100 of the present invention, an electrode line 11 connected to an radio frequency (RF) generator (not shown), and coolant lines 12 are connected to a distribution base 10 that distributes RF waves and coolant. Electrode needles 22 are connected to the distribution base 10 through connection lines 21 to receive RF waves and coolant. The electrode needles 22 are coupled to the front side of an electrode needle base 20. The electrode needle base 20 includes a plurality of dividable bases 23 to which the electrode needles 22 are respectively coupled. When a lesion to be cauterized is large or cauterization should be concentrated, the dividable bases 23 are combined and then used, and when a lesion is small or lesions are located at several positions, the dividable bases 23 are separated and then used.

Although one electrode line 11 is shown in the drawings, as many electrode lines 11 as the number of the electrode needles 22 may be provided. For example, electrode lines 11 may be connected to a multichannel RF electrosurgical unit so that RF waves can be transmitted to the electrode needles 22 according to channels.

For example, three electrode lines 11 may be connected an RF output terminal (RF operation unit) through a 3-in-1 connector to simultaneously supply RF waves to three electrode needles 22.

The electrode needle base 20 is divided into two or more dividable bases 23 to which the electrode needles 22 are respectively coupled.

The electrode needle base 20 is divided into the dividable bases 23 along its length direction. For example, when three electrode needles 22 are necessary, the electrode needle base 20 may be divided into three dividable bases 23. That is, the electrode needle base 20 may include two, three, four, five, or more dividable bases 23 according to operational conditions.

In the following descriptions of the embodiments of the present invention, an exemplary case where three dividable bases 23 are provided will be explained.

A coupling protrusion 25 and a coupling groove 26 are formed on separation surfaces 24 of each of the dividable bases 23 in a manner such that the coupling protrusion 25 and the coupling groove 26 do not interfere with each other.

The coupling groove 26 formed in the separation surface 24 of one dividable base 23 can be coupled with the coupling protrusion 25 formed on the separation surface 24 of another dividable base 23.

In this way, the separation surface 24 of the dividable base 23 can be brought into contact with the separation surface 24 of the other dividable base 23.

The coupling protrusion 25 may be coupled to and detached from the coupling groove 26 by a tight fitting method or a one-touch fitting method.

Widened parts 27 may be formed on both ends of each of the dividable bases 23.

The widened parts 27 may be rounded so that an operator can handle the dividable bases 23 comfortably.

After the dividable bases 23 are coupled to each other, coupling tools 30 may be coupled to the dividable bases 23 in a manner such that the coupling tools 30 can cover and tighten the widened parts 27 so as to prevent separation of the dividable bases 23.

When the dividable bases 23 are coupled, the widened parts 27 may form a sphere shape or the like.

In addition, the electrode needle base structure 100 may be include a guide 40. The guide 40 includes guide stages 42 having different heights, and penetration holes 41 formed through the guide stages 42. The electrode needles 22 may be inserted through the penetration holes 41, respectively.

When the dividable bases 23 are coupled and the electrode needles 22 are simultaneously inserted in the dividable bases 23, the guide 40 guides the electrode needles 22 so that the electrode needles 22 can be uniformly arranged. The electrode needles 22 may be easily inserted into the penetration holes 41 because the electrode needles 22 are sequentially inserted into the penetration holes 41 owing to the guide stages 42 having different heights.

An exemplary use of the combinable electrode needle base structure 100 will now be explained.

First, according to lesion size or scattering, it is determined whether the combinable electrode needle base structure 100 is used in a combined state or a separated state.

The electrode line 11 is connected to an RF generator (not shown) to supply RF waves to the electrode needles 22.

In addition, the coolant lines 12 are connected to a coolant pump (not shown) to supply coolant to the electrode needles 22.

Figure 6:
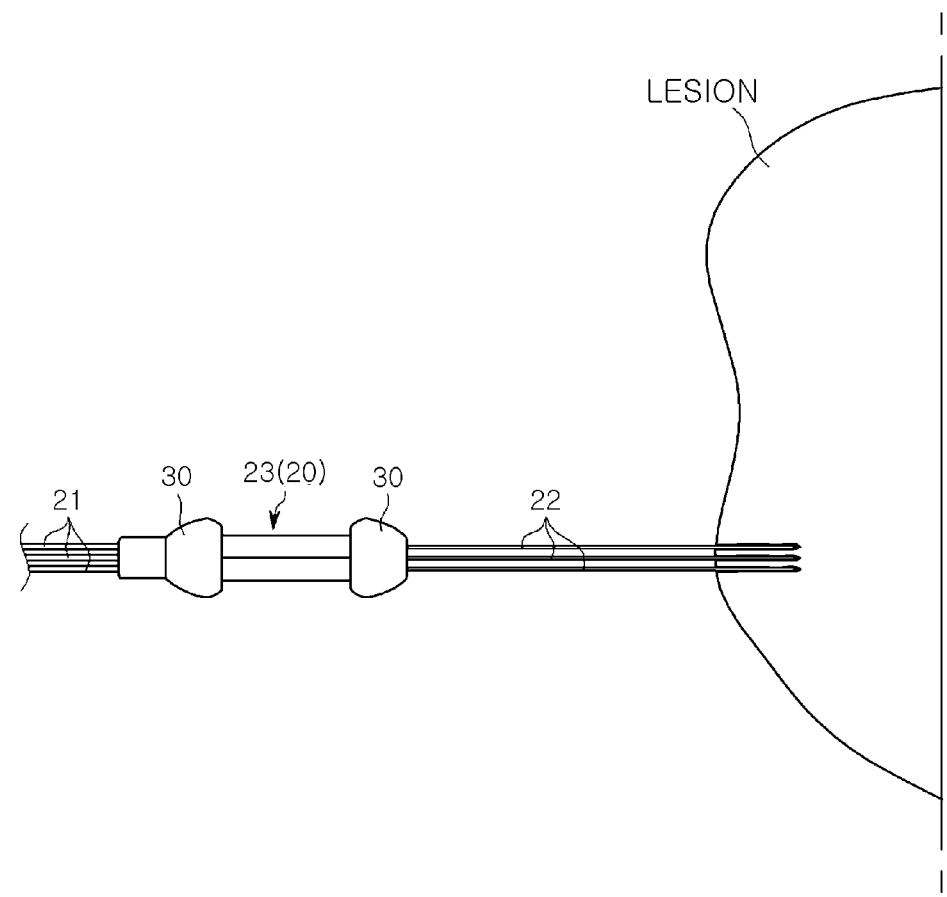
FIG. 6 is a view illustrating an exemplary use of the assembly illustrated in FIG. 5.

As shown in FIG. 6, if a lesion to be cauterized is large, the combinable electrode needle base structure 100 may be used in a combined state by combining the dividable bases 23 of the combinable electrode needle base structure 100.

That is, the dividable bases 23 are combined in a manner such that the coupling protrusion 25 and the coupling groove 26 of one dividable base 23 are coupled to the coupling groove 26 and the coupling protrusion 25 of another dividable base 23.

Then, the coupling tools 30 are coupled to the widened parts 27 of the dividable bases 23 to prevent separation of the combined dividable bases 23 during an operation.

The coupling tools 30 may have an elastic cap shape to prevent the separation of the dividable bases 23 by covering and tightening the widened parts 27 of the dividable bases 23.

The electrode needles 22 are inserted through the penetration holes 41 of the guide 40 so that the distance among the electrode needles 22 can be maintained when the electrode needles 22 are inserted into a patient's body. Thus, the electrode needles 22 may be exactly inserted to an operation position of the patient's body. In this way, the combinable electrode needle base structure 100 may be combined.

After coupling the dividable bases 23 of the combinable electrode needle base structure 100 and inserting the electrode needles 22 into a lesion, the RF generator is operated to supply RF waves and/or coolant to the electrode needles 22 through the connection lines 21, and then the lesion is cauterized.

Figure 7:
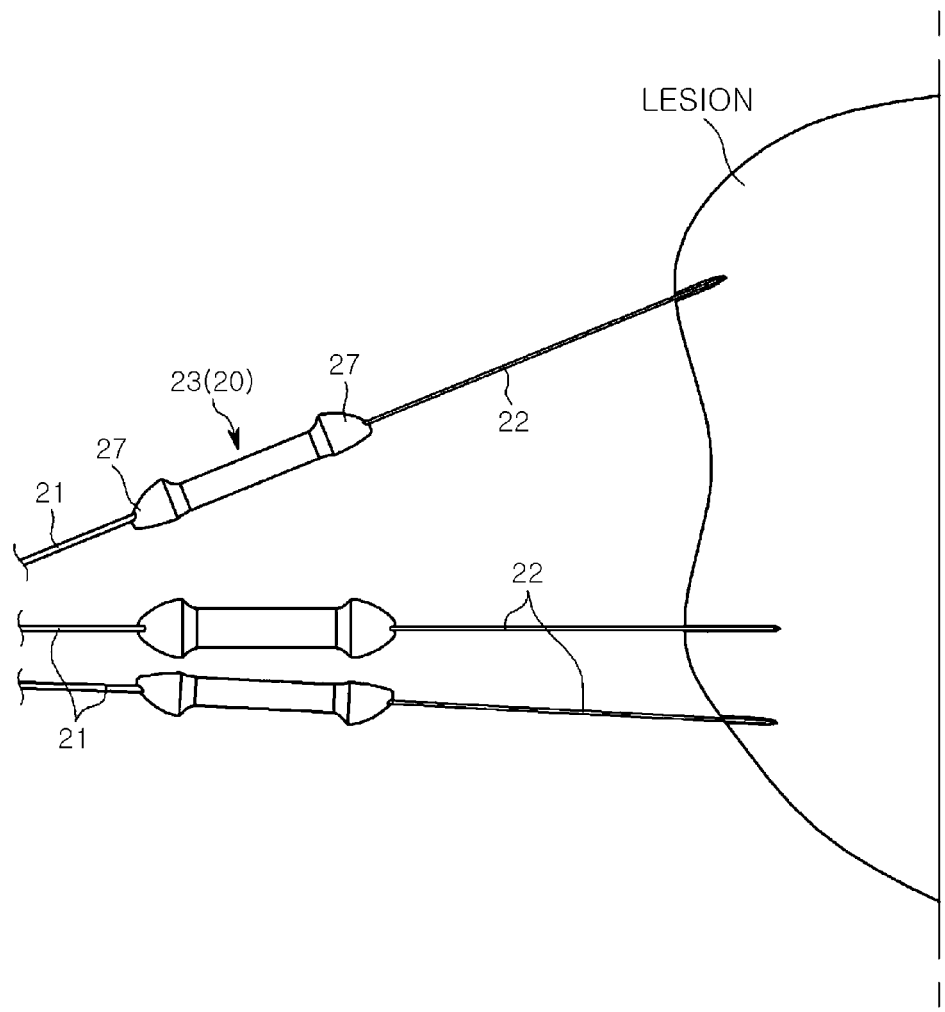
FIG. 7 is a view illustrating an exemplary use of the separated electrode needle base illustrated in FIG. 2.

As shown in FIG. 7, if small lesions are scattered, the guide 40 and the coupling tools 30 may be detached from the dividable bases 23 to separate the dividable bases 23.

Then, the electrode needles 22 coupled to the separated dividable bases 23 are inserted into the scattered small lesions, respectively.

After separating the dividable bases 23 of the combinable electrode needle base structure 100 and inserting the electrode needles 22 into the lesions, the RF generator is operated to supply RF waves and/or coolant to the electrode needles 22 through the connection lines 21, and then the lesions are cauterized.

If it is unnecessary to use all the electrode needles 22, the unnecessary electrode needle(s) 22 may be kept away from patient's body.

In this way, the combinable electrode needle base structure 100 can be used in a combined state or a separated state by coupling or decoupling the coupling protrusions 25 and the coupling grooves 26 of the dividable bases 23.

Figure 8:
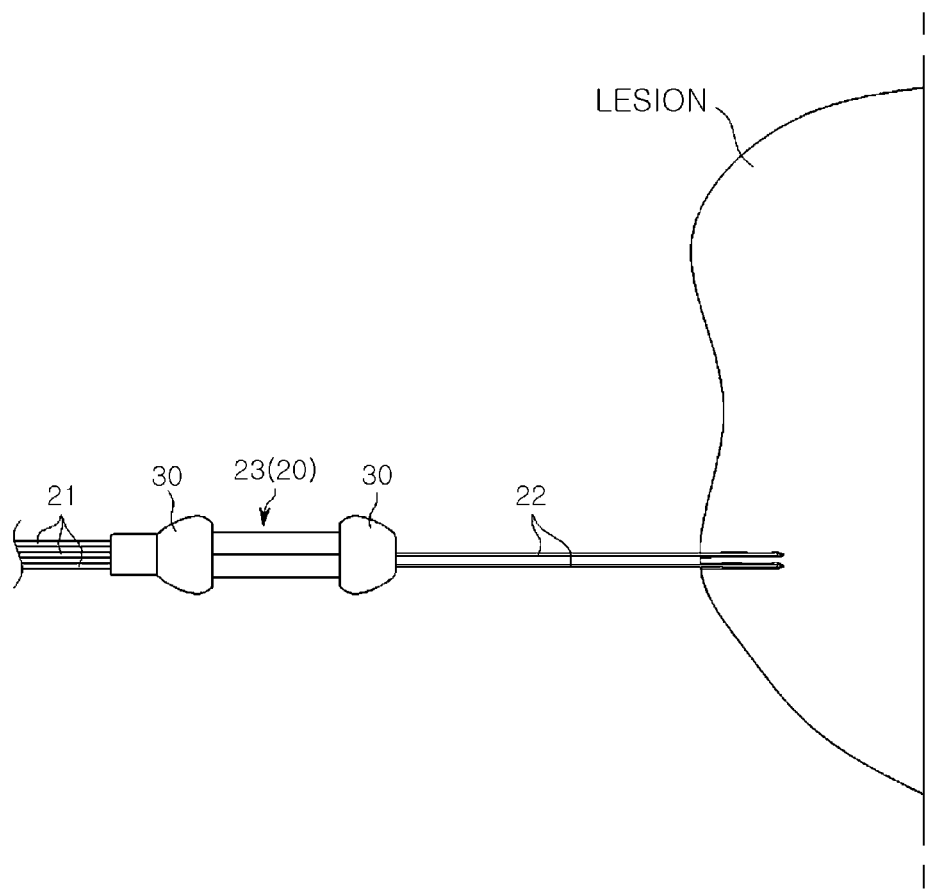
FIG. 8 is a view illustrating another exemplary use of the assembly illustrated in FIG. 5.

For example, as shown in FIG. 8, a dividable base 23 to which an electrode needle 22 is not coupled may be combined with two dividable bases 23 to which electrode needles 22 are respectively coupled, and then the two electrode needles 22 may be used for an operation.

In addition, if any one of the electrode needles 22 is damaged, the damaged electrode needle 22 can be removed from the dividable base 23, and the dividable base 23 can be used together with the other dividable bases 23. That is, the combinable electrode needle base structure 100 can be flexibly used according to conditions.

While the present invention has been shown and described in connection with the exemplary embodiments, it will be apparent to those skilled in the art that modifications and variations can be made without departing from the spirit and scope of the invention as defined by the appended claims.

The invention claimed is:

1. A combinable electrode needle base structure comprising an electrode needle base, the electrode needle base including a front side to which electrode needles are coupled, so as to receive RF waves from RF (radio frequency) generator, wherein the electrode needle base is divided into a plurality of dividable bases to which the electrode needles are respectively coupled, and coupling parts which do not interface with each other are formed on separation surfaces of each of the dividable bases so that the coupling parts of the separation surfaces of one dividable base are coupled to the coupling parts of the separation surfaces of another dividable base, wherein the combinable electrode needle base structure is used in a combined state by coupling the coupling parts of the separation surfaces of one dividable base to the coupling parts of the separation surfaces of another dividable base, or the combinable electrode needle base structure is used in a separated state by decoupling the coupling parts of the separation surfaces of one dividable base from the coupling parts of the separation surfaces of another dividable base, wherein widened parts are formed at both ends of each of the dividable bases, and wherein when the dividable bases are combined, coupling tools are coupled to outer sides of the dividable bases in a manner such that the coupling tools cover and fasten the widened parts of the dividable bases so as to prevent separation of the dividable bases.

2. The combinable electrode needle base structure of claim 1, further comprising a guide, wherein the guide comprises guide stages having different heights, and penetration holes are formed through the guide stages to receive the electrode needles.

* * * * *